(12) United States Patent
Levin et al.

(10) Patent No.: US 9,117,358 B2
(45) Date of Patent: Aug. 25, 2015

(54) METHOD FOR CLASSIFICATION OF EYE CLOSURES

(75) Inventors: Daniel Levin, Göteborg (SE); Lena Westervall, Torslanda (SE); Susanna Leandersson, Särö (SE); Peter Kronberg, Kärna (SE)

(73) Assignee: VOLVO CAR CORPORATION, Gothenburg (SE)

( * ) Notice: Subject to any disclaimer, the term of this patent is extended or adjusted under 35 U.S.C. 154(b) by 450 days.

(21) Appl. No.: 13/558,780

(22) Filed: Jul. 26, 2012

(65) Prior Publication Data

US 2013/0057671 A1 Mar. 7, 2013

(30) Foreign Application Priority Data

Sep. 2, 2011 (EP) ..................................... 11179807

(51) Int. Cl.
*A61B 1/04* (2006.01)
*G08B 21/06* (2006.01)
*A61B 5/00* (2006.01)
*A61B 5/18* (2006.01)
*B60W 40/08* (2012.01)

(52) U.S. Cl.
CPC . *G08B 21/06* (2013.01); *A61B 5/18* (2013.01); *A61B 5/7221* (2013.01); *B60W 40/08* (2013.01); *B60W 2040/0827* (2013.01)

(58) Field of Classification Search
USPC .................. 348/78, 77, 61; 340/575, 576, 449
See application file for complete search history.

(56) References Cited

U.S. PATENT DOCUMENTS

| 6,097,295 | A * | 8/2000 | Griesinger et al. ........... 340/576 |
| 6,154,559 | A | 11/2000 | Beardsley |
| 8,463,487 | B2 * | 6/2013 | Nielsen et al. ............... 701/31.4 |
| 2003/0039378 | A1 | 2/2003 | Yuasa et al. |
| 2005/0073136 | A1 * | 4/2005 | Larsson et al. ................ 280/735 |
| 2008/0180235 | A1 * | 7/2008 | Chang ........................... 340/449 |
| 2008/0238694 | A1 * | 10/2008 | Ishida ........................... 340/575 |
| 2008/0252466 | A1 * | 10/2008 | Yopp et al. .................... 340/576 |
| 2009/0097701 | A1 * | 4/2009 | Nagai et al. ................... 382/100 |
| 2010/0214105 | A1 * | 8/2010 | Manotas, Jr. .................. 340/575 |
| 2011/0060496 | A1 * | 3/2011 | Nielsen et al. .................. 701/33 |
| 2011/0093162 | A1 * | 4/2011 | Nielsen et al. .................. 701/33 |

OTHER PUBLICATIONS

European Search Report for European Application No. EP 11179807.0 dated Feb. 16, 2012.

* cited by examiner

*Primary Examiner* — Paulos M Natnael
(74) *Attorney, Agent, or Firm* — Harness, Dickey & Pierce, P.L.C.

(57) ABSTRACT

The present invention generally relates to a method for improving the reliability of a portion of physiological data from an image sensor monitoring an operator positioned in an operator compartment of a vehicle. An embodiment of the method includes receiving, from the image sensor, physiological data including information relating to at least one of eye, face, head, arms and body motion of the operator, identifying an indication of at least an eyelid closure, eye movement or head movement of the operator based on the physiological data; comparing at least one of the physiological data and a lighting condition within the operator compartment with a set of rules for a current operator status; and classifying the type of eyelid closure, eye movement and/or head movement by correlating the identified eyelid closure, eye movement and/or head movement and a result of the comparison.

12 Claims, 2 Drawing Sheets

US 9,117,358 B2

METHOD FOR CLASSIFICATION OF EYE CLOSURES

PRIORITY STATEMENT

This claims priority under 35 U.S.C. §119 to European Patent Application No. 11179807.0, filed on Sep. 2, 2011, the contents of each of which are hereby incorporated by reference in their entirety.

TECHNICAL FIELD

The present invention relates to improvements in relation to e.g. vehicle implemented methods for automatic drowsiness detection, specifically to a method and corresponding system for classification of eye closures for improving the reliability of e.g. the method for drowsiness detection.

BACKGROUND OF THE INVENTION

Traffic accidents often occur due to driver impairment caused by, for example, drowsiness. In order to prevent accidents caused by driver impairment, it may be vital to provide the driver with a warning message to re-establish the attention of the driver to the surrounding traffic situation, or in a critical situation to advice the driver to take a break or switch to another driver of the vehicle.

Recently, much progress has been made in developing drowsiness detection algorithms that are based on detection of the driver's eye closure with a monitoring sensor, e.g. a camera or the like. These algorithms may be used in an image input unit that, by use of the monitoring sensor, detects the face and eyes of the driver. Hereby, the driver's gaze direction can be detected, e.g. the direction in which the driver of the vehicle is currently looking.

An example of a system having an image input unit can be found in US 2003/039 378. The image input unit of US 2003/039 378 inputs an image including the driver's face area to specify the driver's gaze or face direction. The system generates an input pattern based on the received image input, for determining the driver's gaze or face direction. Moreover, there is provided a dictionary pattern comprising a plurality of stored targets, i.e. positions inside and outside the vehicle which the driver have looked at in the past. The targets may, for example, be the side mirrors, back mirror, infotainment system, etc. Furthermore, the input pattern generated by the system is compared to the stored targets in order to determine the current gaze or face direction of the driver.

However, even though the systems for detecting the driver's eyes have become more and more sophisticated, they do not take in account that there are other factors than drowsiness that may cause the driver to reduce the eye opening size or look away in a certain direction (e.g. due to changing lighting conditions within the vehicle compartment). This may, for example, also be caused by external factors such as direct sunlight, flickering light, headlights from oncoming traffic at nights, etc. Also, if the driver is looking down or sideways, the systems may detect this as an eye closure. There is hence a risk that the driver of the vehicle is provided with a warning message intended for a drowsy driver when, in fact, the driver is fully aware of the situation. It is therefore desirable to provide a method which discriminate between the actual factor(s) of a detected eye closure before a warning message is provided to the driver.

SUMMARY OF THE INVENTION

According to an aspect of the invention, the above is at least partly met by a method for improving the reliability of a portion of physiological data from an image sensor monitoring an operator positioned in an operator compartment of a vehicle, the method comprising receiving, from the image sensor, physiological data comprising information relating to at least one of eye, face, head, arms and body motion of the operator, identifying an indication of at least one of an eyelid closure, eye movement or head movement of the operator based on the physiological data, comparing at least one of the physiological data and a lighting condition within the operator compartment with a predetermined set of rules for a current operator status, and classifying the type of eyelid closure, eye movement and/or head movement by correlating the identified eyelid closure, eye movement and/or head movement and a result of the comparison.

The invention is based on the understanding that by comparing at least one of the physiological data and a lighting condition within the operator compartment with a predetermined set of rules for a current operator status, a robust and reliable method may be provided for determining if e.g. an identified eyelid closure, eye movement and/or head movement is correctly identified or is caused by e.g. measuring data imperfection. For example, if the received information from the image sensor is a flickering movement of the eyes, which is physically impossible, the comparison with the predetermined set of rules may determine that the received information is caused by a measuring data imperfection. This imperfection may be caused by, for instance, that the image sensor at the moment is unable to locate and provide an accurate image of the operator's eyes. According to another example, if the operator of the vehicle suddenly looks over his shoulder to see if he is being overtaken by another vehicle, the image sensor may lose track of the operator's e.g. eyes and instead falsely identify an eyelid closure. Comparison with the predetermined set of rules may than determine that the identified eyelid closure in fact is caused by the driver looking over his shoulder and is not a correct eyelid closure. Hereby, the result of the comparison may be filtered out since it, in this example, was false. According to yet another example, if the operator of the vehicle suddenly is being blinded by e.g. sunlight or the headlights of oncoming vehicles at night (i.e. light entering the compartment from the outside), the operator might turn his head or close his eyelids in a manner that may be identified by the image sensor as an eyelid closure caused by e.g. drowsiness. Hence, comparison with the predetermined set of rules may than filter out the registered eyelid closure since the lighting condition in the vehicle is such that it is likely that the operator has reacted to the bright light than and is thus aware of the surrounding traffic condition.

The wording "physiological data" should in the following be interpreted as all type of data that may be identified by an image based system that identifies e.g. the operator's eyes, face, body, as well as eye gaze direction, eyelid closures, etc. Moreover, the wording "identifying an indication of an eyelid closure" should be interpreted as the image based system identifies that the operator is blinking (fast or slow) or closing his eyes. Furthermore, the lighting condition within the operator compartment may be provided to the image based system by, for example, a separate lighting sensor or the image based system itself. The separate lighting sensor may, for instance, be an infrared sensor (IR), near infrared sensor (NIR), camera with light sensitive characteristics, etc.

Furthermore, comparing the physiological data with the predetermined set of rules for a current operator status may comprise identifying a confidence indication comprised with the physiological data being lower than a predetermined threshold, and providing an error classification of the physiological data if the confidence level is lower than the predetermined threshold. Hereby, an error classification can be made if the physiological data is behaving in a way that is more or less physically impossible, i.e. it is more likely that the image sensor lost track of the positions in the operator's eyes, arms and/or body. "Physically impossible" behaviour may for example be if the physiological data indicates an unnaturally high frequency in head and/or body rotation and the like.

Still further, comparing the physiological data with the predetermined set of rules for a current operator status may comprise identifying a change in a position and/or direction of the face comprised with the physiological data being larger than a predetermined threshold, and providing an error classification of the physiological data if the change in position and/or direction of the face is larger than the predetermined threshold. If, for example, the face of the vehicle operator is directed towards one of the rear view mirrors and the image sensor identifies an eyelid closure, an error classification may be provided since it is more likely that the image sensor lost track of the eyes and that the operator is fully aware of the traffic situation.

According to a further embodiment, comparing the physiological data with the predetermined set of rules for a current operator status comprises estimating a matching level between an eyelid movement, eye movement and/or head movement comprised with the physiological data and a predetermined eyelid movement, eye movement and/or head movement template, and providing an error classification of the physiological data if the matching level is lower than a predetermined threshold.

According to a further embodiment, wherein comparing the physiological data with the predetermined set of rules for a current operator status comprises identifying at least one of eye, face and body movement representing a non-drowsy state of the operator, and providing a non-drowsiness classification of the physiological data if a non-drowsiness state is identified.

According to a further embodiment, comparing the lighting condition within the operator compartment with the predetermined set of rules for a current operator status comprises identifying at least one of an illumination level towards the operator, and a changing lighting condition within the operator compartment.

According to a further embodiment, identifying at least one of the illumination level towards the operator, and the changing lighting condition within the operator compartment comprises analyzing at least one of a contrast level, illumination level, and/or a frequency of illumination level of image data comprised with the physiological data from the image sensor, or from light sensor arranged within the operator compartment of the vehicle.

According to another aspect of the invention there is provided a control system for improving the reliability of a portion of physiological data from an image sensor monitoring an operator positioned in an operator compartment of a vehicle, the control device comprising a control unit configured to receive, from the image sensor, physiological data comprising information relating to at least one of eye, face, head, arms and body motion of the operator, identify an indication of at least an eyelid closure, eye movement or head movement of the operator based on the physiological data, compare at least one of the physiological data and a lighting condition within the operator compartment with a predetermined set of rules for a current operator status, and classify the type of eyelid closure, eye movement and/or head movement by correlating the identified eyelid closure, eye movement and/or head movement and a result of the comparison.

This aspect of the invention provides similar advantages as discussed above in relation to the previous aspect of the invention.

It should be noted that the control system preferably is a driver assistance system for a vehicle, such as a car, a bus or a truck. A more thorough discussion will be given below in relation to the detailed description of the invention. Other types of vehicles are of course possible and within the scope of the invention.

According to a still further aspect of the invention there is provided a computer readable medium embodying a computer program product for improving the reliability of a portion of physiological data from an image sensor monitoring an operator positioned in an operator compartment of a vehicle, the computer program product comprising code configured to, when executed by a processor receiving, from the image sensor, physiological data comprising information relating to at least one of eye, face, head, arms and body motion of the operator, identifying an indication of at least an eyelid closure, eye movement or head movement of the operator based on the physiological data, comparing at least one of the physiological data and a lighting condition within the operator compartment with a predetermined set of rules for a current operator status, and classifying the type of eyelid closure, eye movement and/or head movement by correlating the identified eyelid closure, eye movement and/or head movement and a result of the comparison. Also this aspect of the invention provides similar advantages as discussed above in relation to the previous aspects of the invention.

Further features of, and advantages with, the present invention will become apparent when studying the appended claims and the following description. The skilled addressee realize that different features of the present invention may be combined to create embodiments other than those described in the following, without departing from the scope of the present invention.

BRIEF DESCRIPTION OF THE DRAWINGS

The various aspects of the invention, including its particular features and advantages, will be readily understood from the following detailed description and the accompanying drawings, in which.

DETAILED DESCRIPTION

Figure 1:
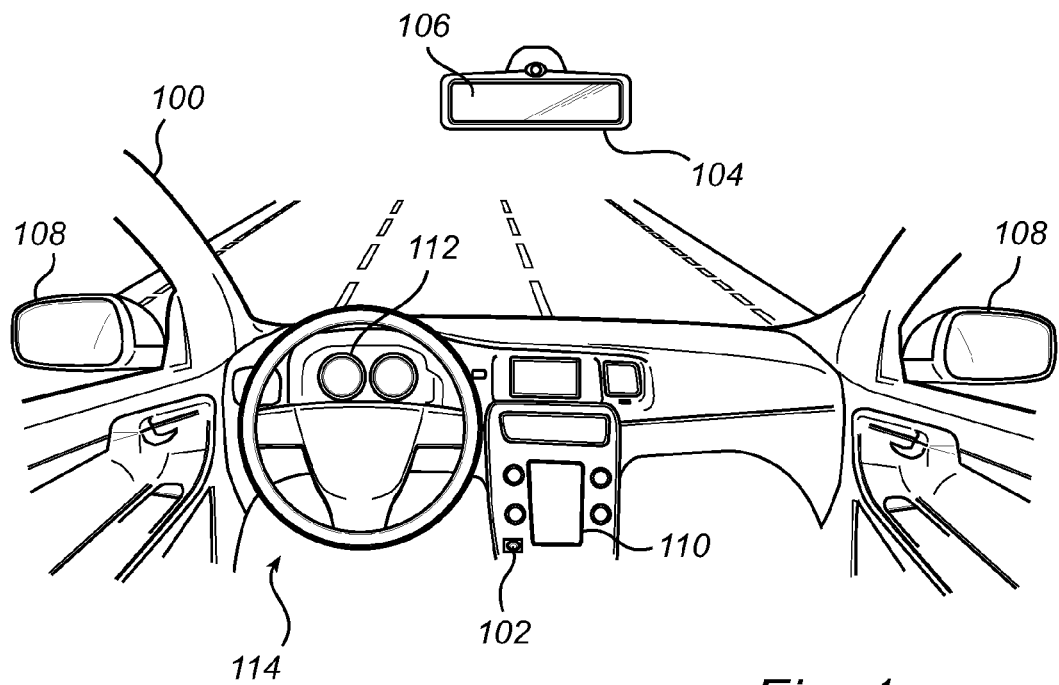
FIG. 1 illustrates a perspective view of the interior of a vehicle, equipped with internal sensors and a plurality of positions within the vehicle normally being gazed by the operator.

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout.

Figure 2:
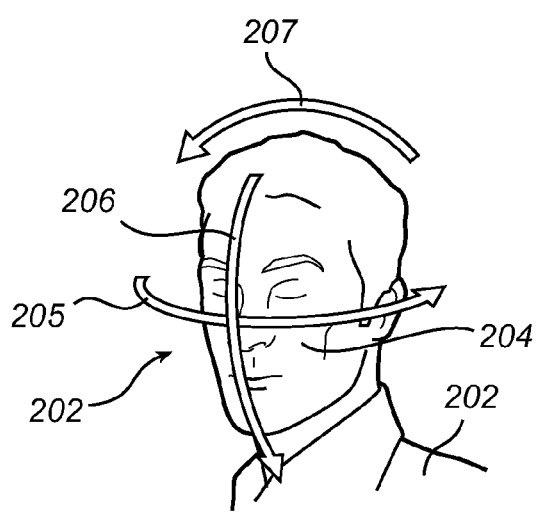
FIG. 2 illustrates a coordinate system of the face of a vehicle operator, and FIG. 3 conceptually illustrates the logical elements of a control system according to a currently preferred embodiment of the invention.

In the following, the present invention is described with reference to a method for improving classification of eye closures of an operator of a vehicle. The vehicle is preferably equipped with interior sensor(s) for retrieving information of the vehicle operator. For the sake of better understanding, reference is now made to FIG. 1, which illustrates an operating compartment 114 of a vehicle, here illustrated as a car 100. The car 100 includes, in the illustrated embodiment, a vehicle operator (not shown) and an internal sensor, here illustrated as a camera system 102. The camera system 102 is arranged to determine the behaviour of the vehicle operator during vehicle operation. Furthermore, the camera system 102 may be arranged to focus on a predetermined number of positions of the operator's face, arms and body. These positions may, for example, be the eyes, eyelids, eyebrows, nose, mouth, cheek, etc. The camera system 102 may be pre-calibrated for a specific operator normally operating the car 100 or being calibrated each time an operator enters the driver seat of the car 100. As the camera system 102 has detected the different positions of the operator's face, an estimation of facial behaviour is possible. The camera system 102 may hence detect, e.g. head and eye direction, head pose, eye saccade, head-eye saccade, eye closure, speed of eye closure, arm motions, body movements, etc. The camera system 102 may also, by use of a coordinate system 202 in connection to the operator's face 204, illustrated in FIG. 2, detect if the head of the operator is rotating to the right or left (yaw) 205, rotating up or down (pitch) 206 or leaning towards the right or left shoulder (roll) 207. The coordinate system 202 of the face 204 is preferably a polar coordinate system with its origin positioned between the eyes of the operator.

Furthermore, the car also comprises an interior light sensor 104, in the described embodiment located behind the interior rear view mirror 106, in the forward direction of the car 100. The exact positioning of the interior light sensor 100 may of course depend on the type of vehicle and its specific interior design. That is, in e.g. a truck there may not be any rear view mirror present and thus the interior light sensor must be placed at another suitable position.

The interior light sensor 104 is arranged to detect oncoming light to the operator compartment, such as bright sunlight or light from the headlights of oncoming traffic at night, which might cause the operator of the vehicle to react. Still further, there are a number of positions in the vehicle compartment which the operator of the vehicle on a normal basis is paying attention to. These are, for example, the exterior rear view mirrors 108, the infotainment system 110, the speed indicator 112, the passenger next to the driver, the gear shift lever, etc.

Figure 3:
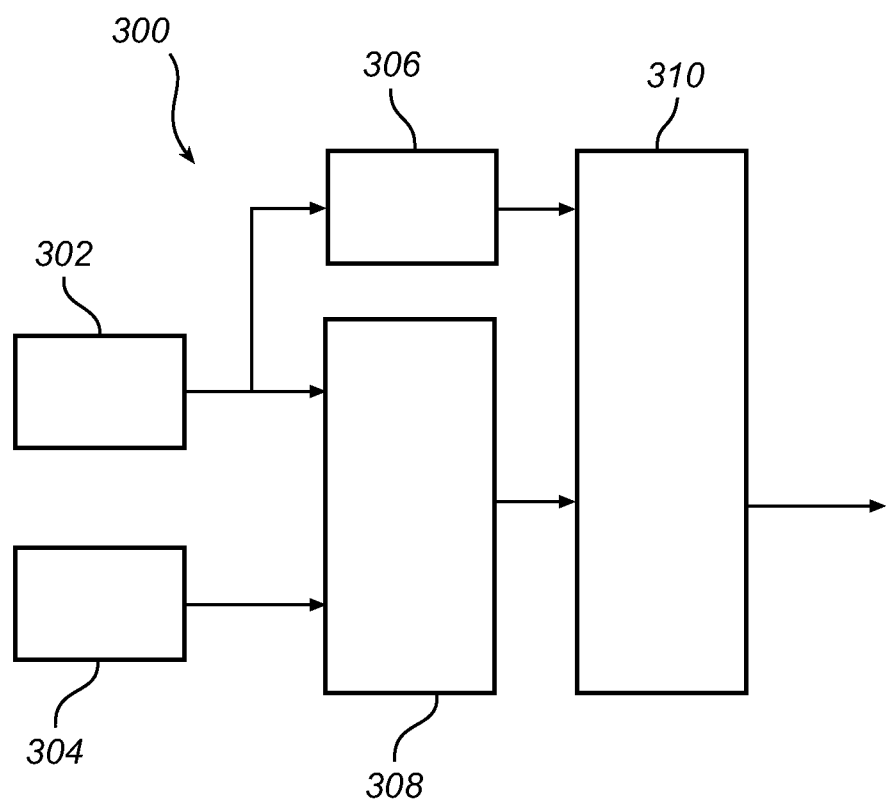

Now referring to FIG. 3, illustrating an exemplary embodiment of a system 300 for providing the method according to the present invention. The system 300 comprises an image sensor 302 which receives information from the camera system 102, an interior light sensor 304, an identification of eyelid closure module 306, a comparison operating module 308 and a drowsiness detection module 310. It should however be noted that the eyelid closure module 306 and the comparison operating module 308 can be one and the same module and are only for illustrating purposes divided from each other. Moreover, the image sensor 302 receives physiological data of the vehicle operator and provides the information to the eyelid closure module 306 and to the comparison operating module 308. The comparison operating module also receives information regarding e.g. operator eyes, arms and body motion from the image sensor 302. Furthermore, the interior light sensor 304 receives information regarding the lighting condition within the operating compartment 114, such as e.g. bright sunlight and headlight from oncoming traffic at night. The interior light sensor 304 also provides the received lighting condition to the comparison operating module 308.

Moreover, when the comparison operating module 308 has received information regarding the lighting condition within the operating compartment 114 as well as the physiological data regarding eyes, arms and body motion of the operator, the comparison operating module 308 compares the information with respect to a predetermined set of rules in order to evaluate the current status of the operator. Thereafter, the drowsiness detection module 310 receives the detected eyelid closure from the eyelid closure module 306 and a classification from the comparison operating module 308 regarding the actual cause(s) of the detected eyelid closure. According to an example, the predetermined set of rules may include the plurality of positions within the operating compartment 114 as described above, such that the system can determine, based on the identified eye-gaze direction and/or face direction, that the operator of the vehicle is currently paying attention to one of these positions. For instance, if the system identifies an eyelid closure of the operator, and at the same time identifies that the operator's face is directed towards the left rear view mirror 108, the system may provide an error classification of the identified eyelid closure, since it is more likely that the operator is fully aware of the situation and that the detection of the eyelids most probably occurred due to the rotation of the operator's head, which the image sensor was unable to correctly follow. Furthermore, the predetermined set of rules may also include certain patterns which are physically possible or impossible to occur. For example, if the image sensor detects that the eyes of the operator is moving irregular up/down or left/right in a way that seems implausible, a predetermined rule may classify the detected behaviour of the eyes as an error.

According to a further example, if the interior light sensor 304 detects a bright light towards the vehicle operator at the same time as the image sensor 302 detects an eyelid closure of the operator, the comparison operating module 306 may provide an error classification of the eyelid closure, since the actual cause is more likely that the vehicle operator squinted with his eyes to compensate for the blinding light. It should be noted that the data from the image sensor 302 may be affected not only at a short (e.g. second(s)) period but over a longer time (e.g. minute(s)) as the image sensor 302 may e.g. lose its calibration due to the changing lighting condition.

Even though the invention has been described with reference to specific exemplifying embodiments thereof, many different alterations, modifications and the like will become apparent for those skilled in the art. Variations to the disclosed embodiments can be understood and effected by the skilled addressee in practicing the claimed invention, from a study of the drawings, the disclosure, and the appended claims. For example, the invention has mainly been described above with reference to a few embodiments. However, as is readily appreciated by the skilled addressee, other embodiments than the ones disclosed above are equally possible within the scope of the invention, as defined by the appended patent claims. For example, the invention is also applicable for trucks, buses, dumpers, wheel loaders and other type of vehicles than the above described car.

In the claims, the word "comprises" does not exclude other elements or steps, and the indefinite article "a" or "an" does not exclude a plurality. A single computer or other unit may fulfil the functions of several items recited in the claims. The mere fact that certain measures are recited in mutually different dependent claims does not indicate that a combination of these measured cannot be used to advantage.

The invention claimed is:

1. A method for improving the reliability of a portion of physiological data from an image sensor monitoring an operator positioned in an operator compartment of a vehicle, the method comprising:
   receiving, from the image sensor, physiological data comprising information relating to at least one of eye, face, head, arms and body motion of the operator;
   identifying an indication of at least one of an eyelid closure, eye movement and head movement of the operator based on the physiological data;
   comparing at least one of the physiological data and a lighting condition within the operator compartment with a set of rules for a current operator status; and
   classifying a type of at least one of eyelid closure, eye movement and head movement by correlating the identified indication of the at least one of eyelid closure, eye movement and head movement and a result of the comparison.

2. Method according to claim 1, wherein comparing the physiological data with the set of rules for a current operator status comprises
   identifying a confidence indication comprised with the physiological data being lower than a threshold, and
   providing an error classification of the physiological data if the confidence level is lower than the threshold.

3. Method according to claim 1, wherein comparing the physiological data with the set of rules for a current operator status comprises identifying a change in at least one of a position and direction of the face comprised with the physiological data being larger than a threshold, and providing an error classification of the physiological data if the change in at least one of position and direction of the face is larger than the threshold.

4. Method according to claim 1, wherein comparing the physiological data with the set of rules for a current operator status comprises
   estimating a matching level between at least one of an eyelid movement, eye movement and head movement comprised with the physiological data and at least one of an eyelid movement, eye movement and head movement template, and
   providing an error classification of the physiological data if the matching level is lower than a threshold.

5. Method according to claim 1, wherein comparing the physiological data with the set of rules for a current operator status comprises identifying at least one of eye, face and body movement representing a non-drowsy state of the operator, and providing a non-drowsiness classification of the physiological data if a non-drowsiness state is identified.

6. Method according to claim 1, wherein comparing the lighting condition within the operator compartment with the set of rules for a current operator status comprises identifying at least one of an illumination level towards the operator, and a changing lighting condition within the operator compartment.

7. Method according to claim 6, wherein identifying at least one of the illumination level towards the operator, and the changing lighting condition within the operator compartment comprises analyzing at least one of a contrast level, illumination level, and a frequency of illumination level of image data comprised with
   the physiological data from the image sensor, or
   from light sensor arranged within the operator compartment of the vehicle.

8. A control system for improving the reliability of a portion of physiological data from an image sensor monitoring an operator positioned in an operator compartment of a vehicle, the control device comprising a control unit configured to:
   receive, from the image sensor, physiological data comprising information relating to at least one of eye, face, head, arms and body motion of the operator;
   identify an indication of at least one of an eyelid closure, eye movement, and head movement of the operator based on the physiological data;
   compare at least one of the physiological data and a lighting condition within the operator compartment with a set of rules for a current operator status; and
   classify the type of at least one of eyelid closure, eye movement and head movement by correlating the identified at least one of eyelid closure, eye movement and head movement and a result of the comparison.

9. Control system according to claim 8, wherein the control unit is further configured to, when comparing the physiological data with the set of rules for a current operator status, identify a confidence indication comprised with the physiological data being lower than a threshold, and providing an error classification of the physiological data if the confidence level is lower than the threshold.

10. Control system according to claim 8, wherein the control unit is further configured to, when comparing the physiological data with the set of rules for a current operator status, identify a change in at least one of a position and direction of the face comprised with the physiological data being larger than a threshold, and providing an error classification of the physiological data if the change in at least one of position and direction of the face is larger than the threshold.

11. Control system according to claim 8, wherein the control system is a driver assistance system for a vehicle.

12. A non-transitory computer readable medium embodying a computer program product for improving the reliability of a portion of physiological data from an image sensor monitoring an operator positioned in an operator compartment of a vehicle, the computer program product comprising code configured to, when executed by a processor:
   receive, from the image sensor, physiological data comprising information relating to at least one of eye, face, head, arms and body motion of the operator;
   identify an indication of at least one of an eyelid closure, eye movement and head movement of the operator based on the physiological data;
   compare at least one of the physiological data and a lighting condition within the operator compartment with a set of rules for a current operator status; and
   classify the type of at least one of eyelid closure, eye movement and head movement by correlating the identified at least one of eyelid closure, eye movement and head movement and a result of the comparison.

* * * * *